United States Patent
Jo et al.

(10) Patent No.: US 11,234,731 B2
(45) Date of Patent: Feb. 1, 2022

(54) ACCESS SHEATH

(71) Applicant: IUCF-HYU (INDUSTRY-UNIVERSITY COOPERATION FOUNDATION HANYANG UNIVERSITY), Seoul (KR)

(72) Inventors: Jung Ki Jo, Seoul (KR); Tae Ho Lim, Seoul (KR); Sung Yul Park, Seoul (KR); Hae Young Park, Seoul (KR); Yong Tae Kim, Seoul (KR); Hong Sang Moon, Seoul (KR); Hong Yong Choi, Seoul (KR); Seung Wook Lee, Seoul (KR); Yoon Je Lee, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 0 days.

(21) Appl. No.: 16/648,406

(22) PCT Filed: Sep. 18, 2018

(86) PCT No.: PCT/KR2018/010972
§ 371 (c)(1),
(2) Date: Mar. 18, 2020

(87) PCT Pub. No.: WO2019/054845
PCT Pub. Date: Mar. 21, 2019

(65) Prior Publication Data
US 2020/0275951 A1 Sep. 3, 2020

(30) Foreign Application Priority Data
Sep. 18, 2017 (KR) .......................... 10-2017-0119793

(51) Int. Cl.
A61B 17/34 (2006.01)
A61B 1/307 (2006.01)
A61B 90/00 (2016.01)

(52) U.S. Cl.
CPC .......... *A61B 17/3423* (2013.01); *A61B 1/307* (2013.01); *A61B 17/3439* (2013.01); *A61B 2090/062* (2016.02)

(58) Field of Classification Search
CPC ........... A61B 17/3423; A61B 17/3439; A61M 25/0668
See application file for complete search history.

(56) References Cited

U.S. PATENT DOCUMENTS 4,738,666 A * 4/1988 Fuqua ............... A61M 25/0023
604/103.05
5,320,605 A * 6/1994 Sahota ................ A61M 25/104
604/101.01
(Continued)

FOREIGN PATENT DOCUMENTS

JP 2006-262932 A 10/2006
JP 2008-512196 A 4/2008
(Continued)

OTHER PUBLICATIONS

International Search Report of PCT/KR2018/010972 dated Dec. 21, 2018 [PCT/ISA/210].

*Primary Examiner* — Anu Ramana
(74) *Attorney, Agent, or Firm* — Sughrue Mion, PLLC

(57) ABSTRACT

An access sheath is provided. The access sheath comprises: an outer sheath extending in one direction and having a cavity formed along a longitudinal axis of the outer sheath; and an inner sheath arranged in the cavity of the outer sheath, and having a plurality of balloons configured to expand, wherein the outer sheath includes: an outer body formed of a first material; and an elastic connection part
(Continued)

formed of a second material which is more flexible than the first material of the outer body, and wherein a diameter of the outer sheath increases by the elastic connection part which expands according to an expansion of the balloons.

6 Claims, 5 Drawing Sheets

(56) References Cited

U.S. PATENT DOCUMENTS

| | | | | |
|---|---|---|---|---|
| 7,749,266 | B2* | 7/2010 | Forster | A61F 2/2418 |
| | | | | 623/2.11 |
| 9,320,508 | B2* | 4/2016 | Carroux | A61M 25/0023 |
| 2014/0088468 | A1* | 3/2014 | Murison | F04B 53/18 |
| | | | | 601/46 |

FOREIGN PATENT DOCUMENTS

| | | |
|---|---|---|
| JP | 2015-534851 A | 12/2015 |
| KR | 10-2011-0045642 A | 5/2011 |
| KR | 10-2014-0051471 A | 5/2014 |
| KR | 10-2016-0021959 A | 2/2016 |
| KR | 10-2016-0066924 A | 6/2016 |
| KR | 10-2017-0061714 A | 6/2017 |

* cited by examiner (A)

(B)

(A)

(B)

ACCESS SHEATH

CROSS REFERENCE TO RELATED APPLICATIONS

This application is a National Stage of International Application No. PCT/KR2018/010972 filed on Sep. 18, 2018, claiming priority based on Korean Patent Application No. 10-2017-0119793 filed on Sep. 18, 2017, the contents of which are incorporated by reference in their entirety.

BACKGROUND OF THE INVENTION

Field of the Invention

The present invention relates to an access sheath, and more particularly, to an access sheath in which the access sheath is inserted into a human body, and a diameter of an outer sheath is extendable.

Description of Related Art

The ureteroscope is an endoscope used for the purpose of diagnosis and treatment from a ureter to a renal pelvis. The ureteroscope includes a rigid ureteroscope and a flexible ureteroscope. A ureteroscope having a small diameter is mainly used for diagnostic purposes, and a ureteroscope having a large diameter may include a separate working passage so as to be used for diagnostic and therapeutic purposes.

In general, a ureteroscopic treatment is widely used to treat ureteral stones, ureter stricture, or the like. The ureteral stones may also be treated with extracorporeal shock wave lithotripsy, but the success rate of the treatment is low when a size of the stone is large or the stone is hard, so that the ureteroscopic treatment is mainly used. The ureter stricture refers to a disease in which a ureter is narrowed, and the ureter may be widened by using an access sheath.

However, an existing access sheath may not be inserted into patients with narrow ureters, so that there is a risk that a surgery may not be performed, or the ureter may have severe damages during the insertion process.

Accordingly, researches on a technology capable of easily inserting an access sheath and reducing side effects due to the insertion have been actively conducted.

BRIEF SUMMARY OF THE INVENTION

One technical object of the present invention is to provide an access sheath which is easily inserted into patients with narrow ureters.

In addition, another object of the present invention is to provide an access sheath capable of minimizing ureteral damages in a ureter insertion process.

The technical objects of the present invention are not limited to the above-described objects.

In order to achieve the technical objects, the present invention provides an access sheath.

According to one embodiment, the access sheath includes: an outer sheath extending in one direction and having an insertion space formed in a longitudinal direction; and an inner sheath introduced into the insertion space of the outer sheath, and having a plurality of balloons, wherein the outer sheath includes: an outer body having a cutting gap formed in the longitudinal direction of the outer sheath; and an elastic connection part filled in the cutting gap so as to connect a cutting area of the outer body, and formed of an elastic material which is more flexible than a material of the outer body, and wherein the elastic connection part expands and a diameter of the outer body increases according to an expansion of the balloons.

According to one embodiment, the access sheath may further include a fixing member provided at one end of the outer sheath, wherein the fixing member may fix the outer body to maintain the diameter of the outer body increased by the expansion of the balloons.

According to one embodiment, the cutting gap may be parallel to the longitudinal direction of the outer sheath.

According to one embodiment, the cutting gap may be formed in a spiral shape along a circumference of the outer body.

According to one embodiment, the elastic connection part may be configured as a combination of a plurality of unit connection parts consecutively provided along the cutting gap, and the unit connection parts may be arranged such that adjacent unit connection parts may partially overlap each other.

According to one embodiment, the outer body may be formed of plastic, and the elastic connection part may be formed of silicone.

In the access sheath according to the present invention, after the outer sheath and the inner sheath are inserted into the ureter, the diameter of the outer sheath increases according to the expansion of the balloons provided on the inner sheath, so that the ureter can be widened. Therefore, the access sheath according to the present invention may have a diameter smaller than a diameter of the existing access sheath, so that the access sheath can be easily inserted even into a narrow ureter, and ureteral damages can be minimized during the insertion process.

DETAILED DESCRIPTION OF THE INVENTION

Figure 1:
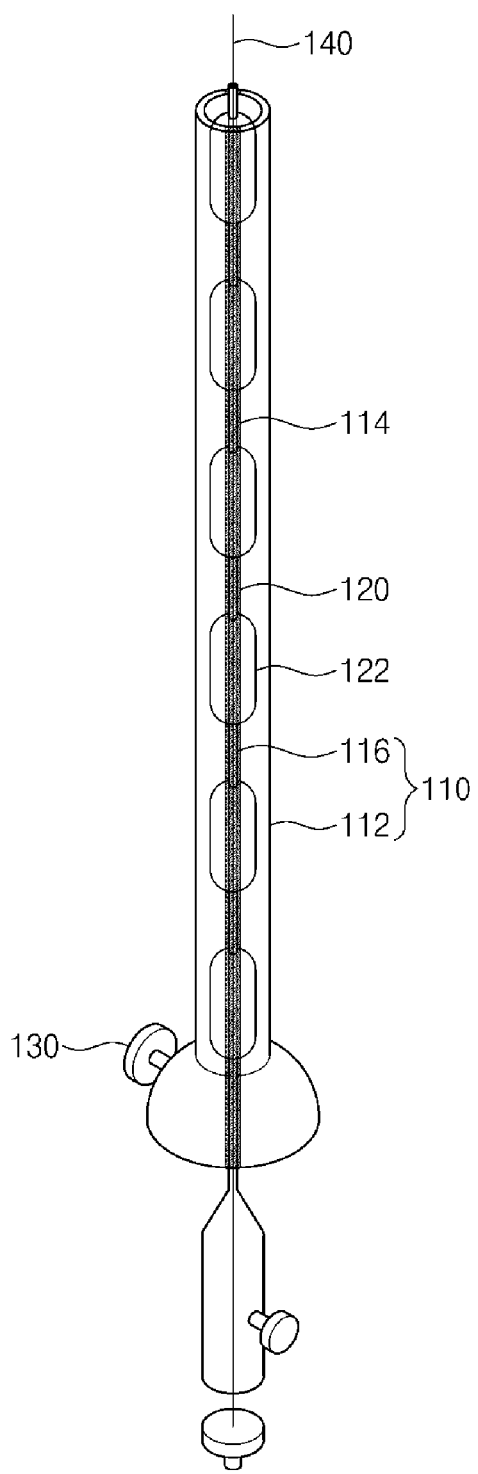
FIG. 1 is a view for describing an access sheath according to a first embodiment of the present invention.

According to the present invention, the access sheath includes: an outer sheath extending in one direction and having an insertion space formed in a longitudinal direction; and an inner sheath introduced into the insertion space of the outer sheath, and having a plurality of balloons, wherein the outer sheath includes: an outer body having a cutting gap formed in the longitudinal direction of the outer sheath; and an elastic connection part filled in the cutting gap so as to connect a cutting area of the outer body, and formed of an elastic material which is more flexible than a material of the outer body, and wherein the elastic connection part expands and a diameter of the outer body increases according to an expansion of the balloons.

Hereinafter, exemplary embodiments of the present invention will be described in detail with reference to the accompanying drawings. However, the technical idea of the present invention is not limited to the embodiments, but may be realized in different forms. The embodiments introduced herein are provided to sufficiently deliver the spirit of the present invention to those skilled in the art so that the disclosed contents may become thorough and complete.

When it is mentioned in the present disclosure that one element is on another element, it means that a first element may be directly formed on a second element, or a third element may be interposed between the first element and the second element. Further, in the drawings, thicknesses of membranes and areas are exaggerated for efficient description of the technical contents.

In addition, in the various embodiments of the present disclosure, the terms such as first, second, and third are used to describe various elements, but the elements are not limited to the terms. The terms are used only to distinguish one element from another element. Accordingly, an element mentioned as a first element in one embodiment may be mentioned as a second element in another embodiment. The embodiments described and illustrated herein include their complementary embodiments. Further, the term "and/or" in the present disclosure is used to include at least one of the elements enumerated before and after the term.

In the present disclosure, the terms of a singular form may include plural forms unless the context clearly indicates otherwise. Further, the terms such as "including" and "having" are used to designate the presence of features, numbers, steps, elements, or combinations thereof described in the present disclosure, and shall not be construed to preclude any possibility of presence or addition of one or more other features, numbers, steps, elements, or combinations thereof.

Further, in the following description of the present invention, a detailed description of known functions and configurations incorporated herein will be omitted when it may make the subject matter of the present invention unnecessarily unclear.

Figure 2:
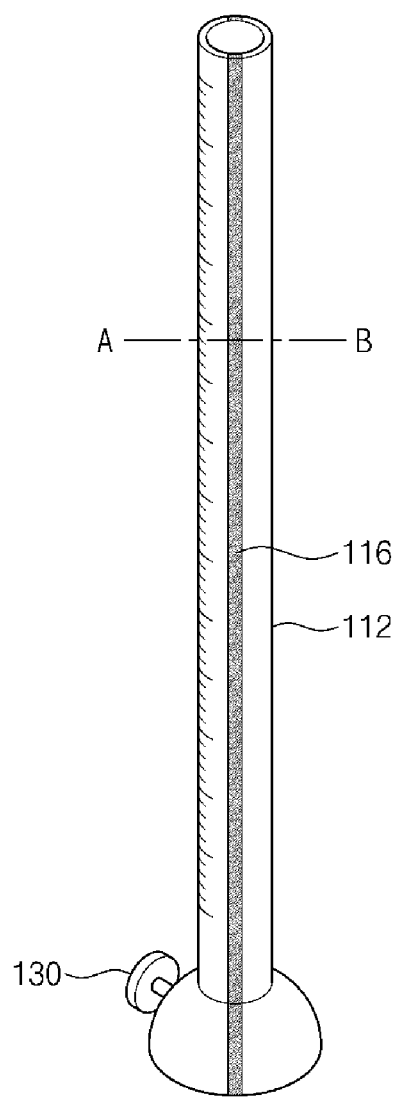
FIG. 2 is a view for describing an outer sheath of the access sheath according to the first embodiment of the present invention.
Figure 2:
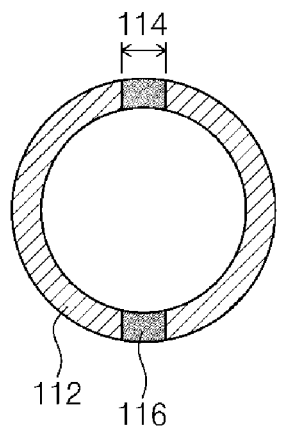
Figure 3:
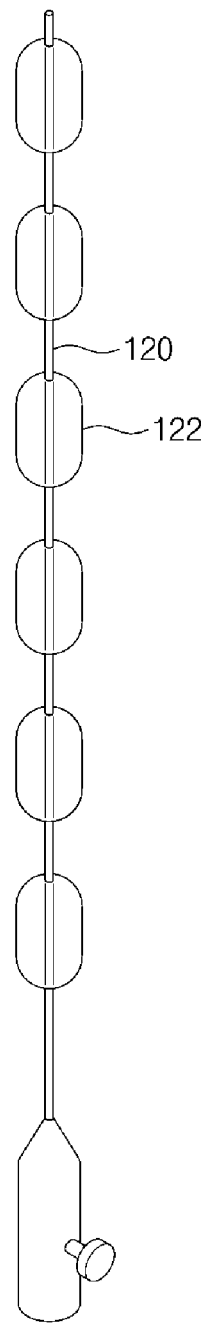
FIG. 3 is a view for describing an inner sheath of the access sheath according to the first embodiment of the present invention.
Figure 3:
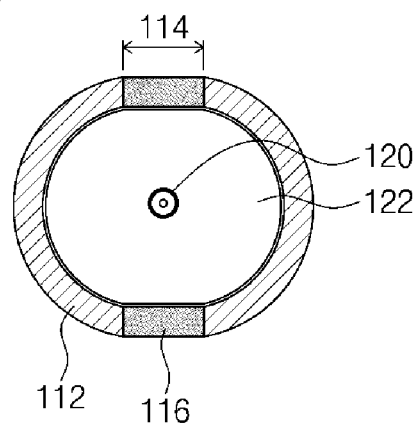

FIG. 1 is a view for describing an access sheath according to a first embodiment of the present invention, FIG. 2 is a view for describing an outer sheath of the access sheath according to the first embodiment of the present invention, and FIG. 3 is a view for describing an inner sheath of the access sheath according to the first embodiment of the present invention.

First, referring to FIGS. 1 and 2, an access sheath 100 may include an outer sheath 110, an inner sheath 120, a fixing member 130, and a guide wire 140.

The outer sheath 110 may extend long in one direction and have an insertion space formed in a longitudinal direction. The outer sheath 110 may include an outer body 112 and an elastic connection part 116.

The outer body 112 is a tube formed in the longitudinal direction of the outer sheath 110, and may be formed therein with the insertion space. In addition, a cutting gap 114 may be formed in the outer body 112. The cutting gap 114 may be formed in the longitudinal direction of the outer sheath 110 from one end to an opposite end of the outer sheath 110. A side part of the outer body 112 may be cut by the cutting gap 114. According to an embodiment, the cutting gap 114 may be parallel to the longitudinal direction of the outer sheath 110. According to the embodiment, two cutting gaps 114 may be formed in the outer body 112, and the outer body 112 may be divided into two areas by the cutting gaps 114.

The elastic connection part 116 may be filled in the cutting gaps 114, and may connect a cutting area of the outer body 112. The elastic connection part 116 may be formed of an elastic material which is more flexible than a material of the outer body 112. According to an embodiment, both the outer body 112 and the elastic connection part 116 may be formed of silicone, and the elastic connection part 116 may have a more flexible composition as compared with the outer body 112. Alternatively, the outer body 112 may be formed of plastic, and the elastic connection part 116 may be formed of silicone.

A graduation may be formed on the outer body 112. When an operator inserts the access sheath 100 into a ureter of a patient, the graduation may be provided to measure a depth by which the access sheath 100 is inserted.

The inner sheath 120 may be provided as a tube which is introduced into the insertion space of the outer sheath 110. A plurality of balloons 122 may be provided on an outer circumferential surface of the inner sheath 120 in a longitudinal direction of the inner sheath 120. The balloons 122 may expand and contract according to air injected from an outside. When the balloons 122 expand, an expanding force may be transmitted to the outer sheath 110, and the elastic connection part 116 extends, so that a diameter of the outer body 122 may be increased.

The fixing member 130 may be provided at one end of the outer sheath 110. The fixing member 130 may fix the outer body 112 to maintain the diameter of the outer body 112 increased by the expansion of the balloons 122.

The guide wire 140 is a wire having a diameter smaller than a diameter of the inner sheath 120, and may be inserted into the ureter before the outer sheath 1120 and the inner sheath 120 in a ureteroscopic treatment. Since the guide wire 140 has a small diameter, even the insertion into a narrow ureter can be facilitated. The guide wide 140 may guide a ureter insertion path for the outer sheath 110 and the inner sheath 120.

Figure 4:
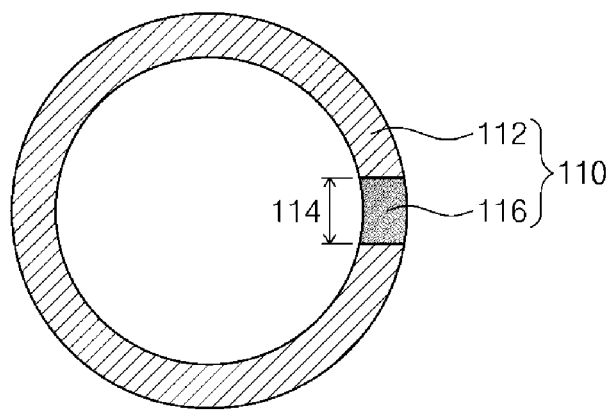
FIG. 4 is a sectional view for describing an outer sheath of an access sheath according to a second embodiment of the present invention.

FIG. 4 is a sectional view for describing an outer sheath of an access sheath according to a second embodiment of the present invention.

Referring to FIG. 4, the outer body 112 may include a single cutting gap 114, and an elastic connection part 116 may be filled in the cutting gap 114.

Figure 5:
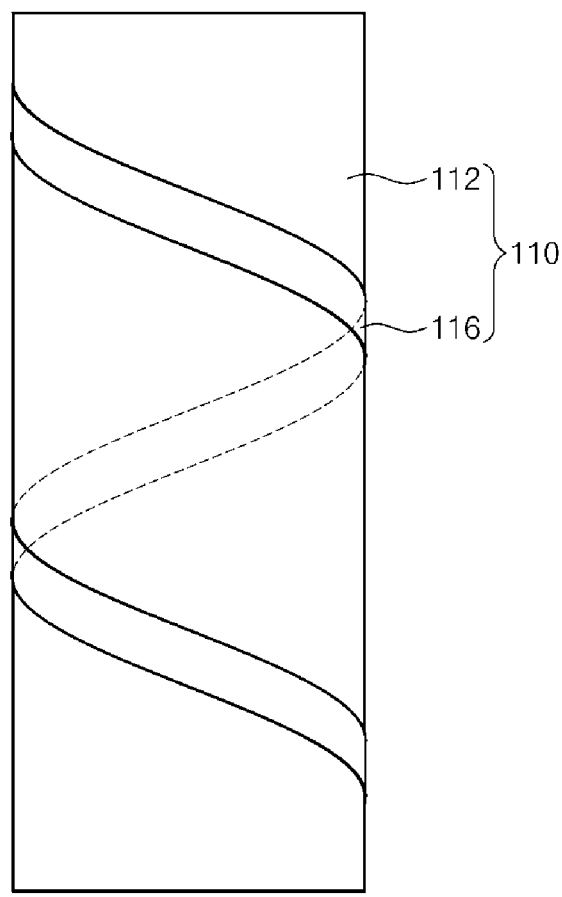
FIG. 5 is a view for describing an outer sheath of an access sheath according to a third embodiment of the present invention.
Figure 6:
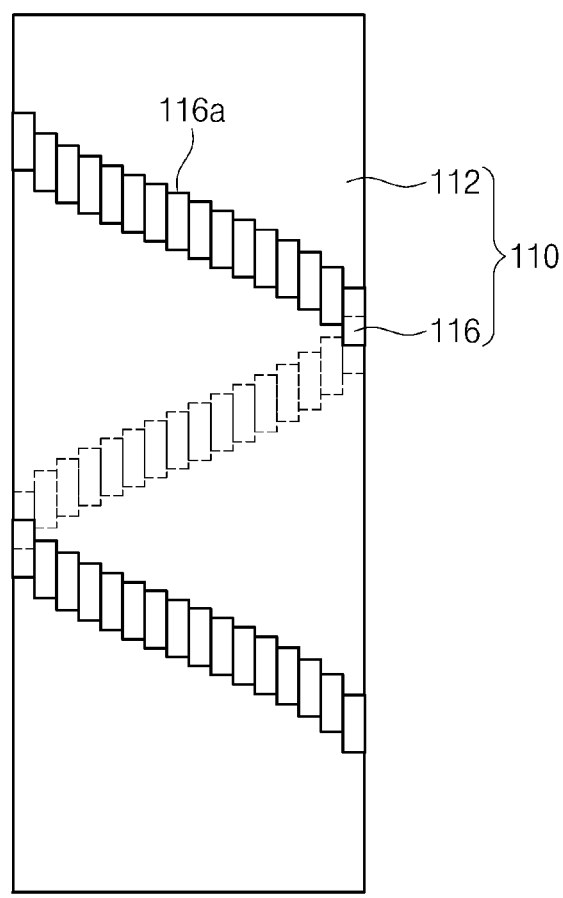
FIG. 6 is a view for describing an outer sheath of an access sheath according to a fourth embodiment of the present invention.

FIG. 5 is a view for describing an outer sheath of an access sheath according to a third embodiment of the present invention, and FIG. 6 is a view for describing an outer sheath of an access sheath according to a fourth embodiment of the present invention.

Referring to FIG. 5, the outer sheath 110 may include an outer body 112 and an elastic connection part 116, and the outer body 112 may include a cutting gap formed in a spiral shape along a circumference of the outer body 112. Therefore, the outer sheath 110 may include the elastic connection part 116 having a spiral shape.

Referring to FIG. 6, the outer sheath 110 may include an outer body 112 and an elastic connection part 116 having a spiral shape. In detail, the spiral-shaped elastic connection part 116 may be configured as a combination of a plurality of unit connection parts 116a consecutively provided along the cutting gap, and the unit connection parts 116a may be arranged such that adjacent unit connection parts 116a partially overlap each other.

The elastic connection part 116 of the access sheath 100 according to the third and fourth embodiments of the present invention may have a spiral shape, so that the outer sheath 100 may uniformly expand in a radial direction when the balloons expand. Accordingly, the access sheath 100 may expand the narrow ureter so that the ureter may have a uniform diameter.

In the access sheath 100 according to the present invention, after the outer sheath 110 and the inner sheath 120 are inserted into the ureter, the balloons 122 provided on the inner sheath 120 may expand, and the diameter of the outer sheath 110 increases, so that the ureter can be widened. Accordingly, the access sheath 100 according to the present invention may have a smaller diameter than an existing access sheath which has a diameter that may not vary. Since the outer sheath 110 is inserted with a narrow diameter, even the insertion into a narrow ureter can be facilitated, and ureteral damages can be minimized during the insertion process.

Although the access sheath 100 has been described in the above embodiments as being applied to a treatment for expanding a narrowed ureter, an application scope of the access sheath 100 according to the present invention is not limited thereto. The access sheath 100 according to the present invention can be applied to various treatments for expanding tubular tissues in a body.

Although the exemplary embodiments of the present invention have been described in detail, the scope of the present invention is not limited to a specific embodiment, and should be interpreted by the appended claims. In addition, it should be understood by those skilled in the art to which the invention pertains that various changes and modifications can be made without departing from the scope of the present invention.

The access sheath according to the present invention can be inserted into the human body, and the diameter of the outer sheath is extendable.

The invention claimed is:

1. An access sheath comprising:
an outer sheath extending in one direction and having a cavity formed along a longitudinal axis of the outer sheath; and
an inner sheath arranged in the cavity of the outer sheath, and having a plurality of balloons configured to expand,
wherein the outer sheath includes:
an outer body formed of a first material; and
an elastic connection part formed of a second material which is more flexible than the first material of the outer body, and
wherein a diameter of the outer sheath increases when the elastic connection part expands according to an expansion of the balloons.

2. The access sheath of claim 1, further comprising a fixing member provided at one end of the outer sheath, and configured to restrict an increase in the diameter of the outer body by the expansion of the balloons.

3. The access sheath of claim 1, wherein the elastic connection part extends in parallel to the longitudinal axis of the outer sheath.

4. The access sheath of claim 1, wherein the elastic connection part has a spiral shape formed around the longitudinal axis of the outer sheath.

5. The access sheath of claim 4, wherein the elastic connection part includes a plurality of unit connection parts which are formed of the second material and connected to one another such that the spiral shape is formed.

6. The access sheath of claim 1, wherein the outer body is formed of plastic, and the elastic connection part is formed of silicone.

* * * * *